(12) United States Patent
Fendrock

(10) Patent No.: US 6,514,460 B1
(45) Date of Patent: Feb. 4, 2003

(54) LUMINOUS GLUCOSE MONITORING DEVICE

(75) Inventor: Charles Fendrock, Sudbury, MA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/362,205

(22) Filed: Jul. 28, 1999

(51) Int. Cl.$^7$ ............................................... G01N 21/00
(52) U.S. Cl. ..................... 422/55; 422/68.1; 422/99; 436/66; 436/95; 436/164; 436/174; 250/461.1; 250/462.1
(58) Field of Search ............................... 422/58, 61, 55, 422/68.1, 73, 99, 104; 436/55, 66, 95, 164, 165, 174, 177, 178, 179; 250/461.2, 463.1, 462.1, 466.1, 467.1

(56) References Cited

U.S. PATENT DOCUMENTS

| | | | | |
|---|---|---|---|---|
| 2,441,559 A | * | 5/1948 | Burrell | |
| 5,073,843 A | * | 12/1991 | Magee | 362/84 |
| 5,352,351 A | | 10/1994 | White et al. | |
| 5,366,609 A | | 11/1994 | White et al. | |
| 5,405,511 A | | 4/1995 | White et al. | |
| 5,458,311 A | * | 10/1995 | Holbrook | 248/309.1 |
| 5,565,085 A | | 10/1996 | Ikeda et al. | |
| 5,597,532 A | * | 1/1997 | Connolly | 422/58 |
| 5,628,890 A | | 5/1997 | Carter et al. | |
| 5,665,215 A | * | 9/1997 | Bussman et al. | 204/403 |
| 5,711,595 A | * | 1/1998 | Gerbe | 362/84 |
| 5,752,761 A | * | 5/1998 | Pietruczynik et al. | 362/84 |
| 5,786,584 A | * | 7/1998 | Button et al. | 235/462 |
| 5,872,713 A | * | 2/1999 | Douglas et al. | 364/413.09 |
| 5,925,012 A | | 7/1999 | Murphy-Chutorian et al. | |
| 5,989,917 A | * | 11/1999 | McAleer et al. | 436/46 |
| 5,995,236 A | * | 11/1999 | Roth et al. | 356/445 |

FOREIGN PATENT DOCUMENTS

| | | |
|---|---|---|
| GB | 2154003 | 8/1985 |
| WO | 92/15373 | 9/1992 |
| WO | 99/18848 | 4/1999 |

OTHER PUBLICATIONS

Encyclopedia of Chemical Technology, vol. 6, 4$^{th}$ Edition, John Wiley & Sons, Inc. (1993) pp. 606–669.
Encyclopedia of Chemical Technology, vol. 15, 4$^{th}$ Edition, John Wiley & Sons, Inc. (1995) pp. 403–407.

* cited by examiner

Primary Examiner—Jill Warden
Assistant Examiner—Dwayne K Handy
(74) Attorney, Agent, or Firm—David L. Weinstein

(57) ABSTRACT

A glucose monitoring device suitable for use in total darkness or in limited light environment. The glucose monitoring device comprises a housing, which encloses the components of the device that determine the blood glucose level of a blood sample on a test strip. The exterior surface of the housing comprises a phosphorescent material. The portion of the test strip where the blood sample is to be applied can be illuminated by a light. The area of the glucose monitoring device where the test strip is inserted into the device can also be illuminated by a light. The display of the device, i. e., the area of the glucose monitoring device where the result is read, is also illuminated by a light.

7 Claims, 4 Drawing Sheets

(2 of 4 Drawing Sheet(s) Filed in Color)

LUMINOUS GLUCOSE MONITORING DEVICE

BACKGROUND OF THE INVENTION

1. Field of the Invention

This invention relates to glucose monitoring devices, more particularly, glucose monitoring devices for use in conditions of dim light or total darkness.

2. Discussion of the Art

The prevalence of diabetes has been increasing markedly in the world. At this time, diagnosed diabetics represented about 3% of the population of the United States. It is believed that the total actual number of diabetics in the United States is over 16,000,000. Diabetes can lead to numerous complications, such as, for example, retinopathy, nephropathy, and neuropathy.

The most important factor for reducing diabetes-associated complications is the maintenance of an appropriate level of glucose in the blood stream. The maintenance of the appropriate level of glucose in the blood stream may prevent and even reverse many of the effects of diabetes.

In order to use a glucose monitoring device, a sample of blood from an individual must first be obtained by any of a variety of methods, such as by needle or lancet. The individual then inserts a test strip carrying reagents into a blood glucose monitoring device, in which device blood glucose level is determined by a change in reflectance or a change in current of the test strip. The individual then applies the sample of blood to the test strip. The blood reacts with the reagents and causes a change in reflectance or a change in current of the test strip, thereby indicating the concentration of glucose in the sample of blood. There are numerous devices currently available for diabetics to monitor the concentration of glucose in blood.

Numerous glucose monitoring devices are commercially available. For example, some of the most popular glucose monitoring devices are sold under the following trade names: "PRECISION QID", "MEDISENSE 2", "EXACTECH", all of which are available from Abbott Laboratories, "SURESTEP", "ONE TOUCH", all of which are available from Johnson & Johnson, "GLUCOMETER ELITE", available from Bayer, and "ACCUCHECK", available from Boehringer Mannheim. The foregoing glucose monitoring devices employ the principles previously described, i. e., measuring a change in reflectance or a change in current. At times, blood glucose level must be monitored under conditions of total darkness or limited light. For example, if blood glucose level is monitored in the middle of the night, it is likely that the room where the measurement is taken will be in total darkness. If blood glucose level is monitored at dusk, it is likely that the room where the measurement is taken will be in dim light. As indicated previously, one of the effects of diabetes is retinopathy. In conditions of total or partial darkness, an individual suffering from retinopathy may have difficulty in locating the glucose monitoring device or in using the glucose monitoring device once it is located. When testing in low light or in complete darkness, one has to turn on the light, move to an area of more light, or perform the assay in the dark. One glucose monitoring device, "ACCUCHECK COMPLETE", has side lighting of the LCD display, but no other illumination.

Therefore, it would be desirable to provide a glucose monitoring device that can be easily located in conditions of complete or partial darkness and that can be used in conditions of complete or partial darkness after it is located.

SUMMARY OF THE INVENTION

This invention provides a glucose monitoring device suitable for use in total darkness or in limited light environment. The glucose monitoring device comprises a housing, which encloses the components of the device that determine the blood glucose level of a blood sample on a test strip. The exterior surface of the housing comprises a phosphorescent material. The portion of the test strip where the blood sample is to be applied can be illuminated by a light. The area of the glucose monitoring device where the test strip is inserted into the device can also be illuminated by a light. The light for illuminating the test strip can also provide the incident radiation to bring about light emission by the phosphorescent material. The display of the device, i. e., the area of the glucose monitoring device where the result is read, is also illuminated by a light.

This invention addresses at least three problems typically encountered by a diabetic who is suffering from retinopathy. The housing allows the patient to locate the glucose monitoring device in partial or total darkness. The light for illuminating the test strip enables the patient to easily insert the test strip into a port in the housing of the glucose monitoring device in partial or total darkness. The lighting of the display allows the patient to read the test result in partial or total darkness.

BRIEF DESCRIPTION OF THE DRAWINGS

The patent or application file contains at least one drawing executed in color. Copies of this patent or patent application publication with color drawing(s) will be provided by the Patent and Trademark Office upon request and payment of the necessary fee.

DETAILED DESCRIPTION

As used herein, the term "phosphorescent" means the property of a substance that persistently emits light following exposure to and removal of incident radiation. The phrase "phosphorescent material" means a substance that persistently emits light following exposure to and removal of incident radiation. The term "light" means (1) electromagnetic radiation that has a wavelength in the range of from about 390 to about 770 nm and that may be perceived by the unaided, normal human eye or (2) a source of light, e. g., a light emitting diode, depending upon the context.

Figure 1:
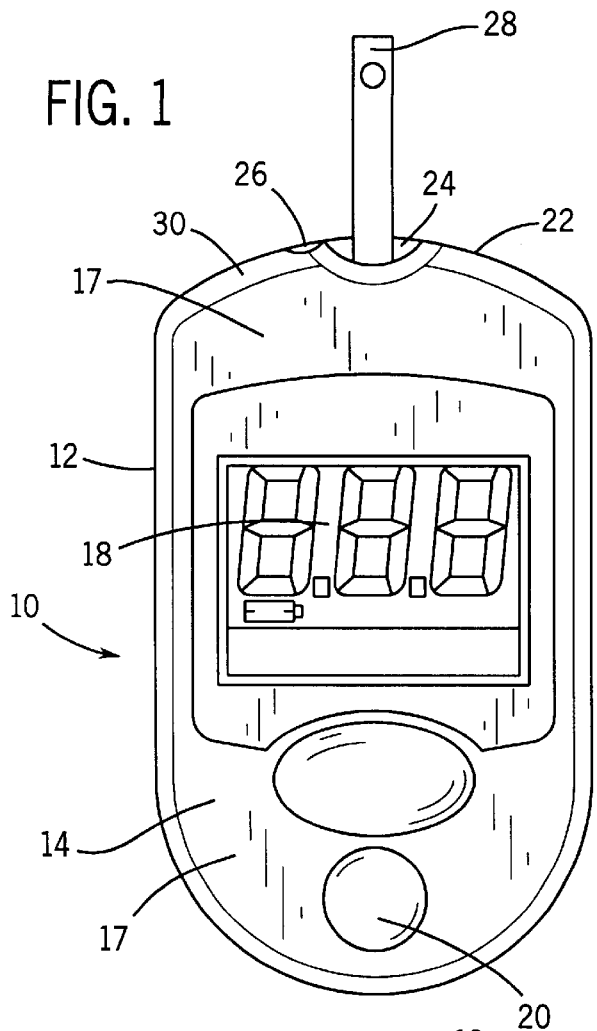
FIG. 1 is a plan view of a glucose monitoring device suitable for use in this invention.
Figure 2:
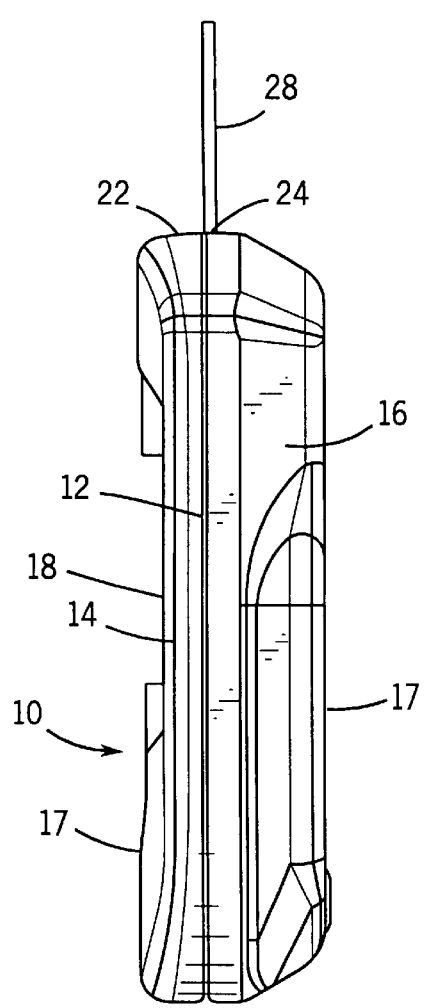
FIG. 2 is a side view in elevation of the glucose monitoring device of FIG. 1.
Figure 3:
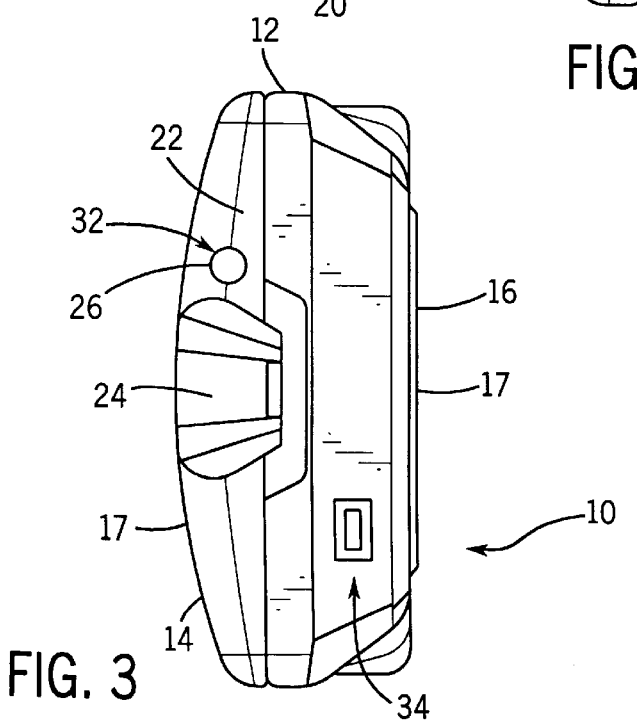
FIG. 3 is a view showing the top of the glucose monitoring device of FIG. 1.
Figure 4:
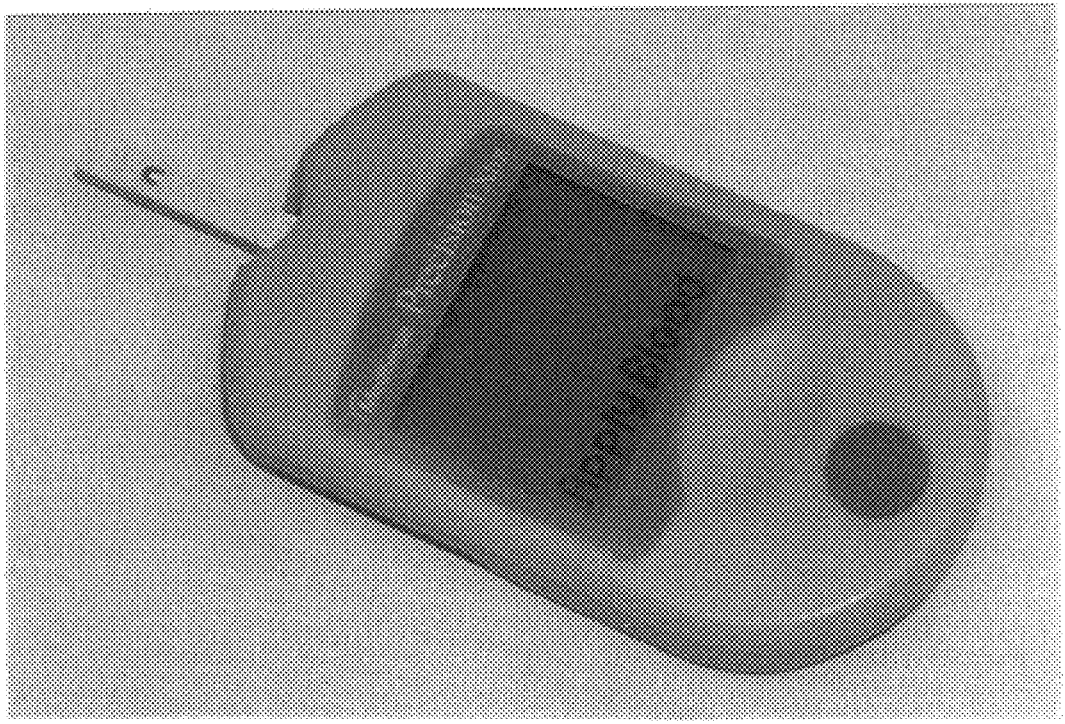
FIG. 4 is a photograph showing a glucose monitoring device suitable for use in the present invention.

Referring now to FIGS. 1, 2, and 3, a glucose monitoring device 10 comprises a housing 12. The housing 12 comprises a front panel 14 and a rear panel 16. The panels are preferably formed from a polymeric material, which is formed or molded to the desired shape. Polymeric materials suitable for forming 25 or molding the panels 14 and 16 are well-known to those of ordinary skill in the art. Within the housing 12 are contained the electrical and mechanical components of the glucose monitoring device. These components are well known to one of ordinary skill in the art and are described in more detail in, for example, U. S. Pat. Nos. 5,352,351; 5,366,609; 5,405,511; 5,565,085, all of which are incorporated herein by reference. The housing 12 of the device 10 has an exterior surface 17. The exterior surface 17 of the housing 12 is visible to the user; the electrical and mechanical components within the housing 12 are not visible to the user, unless the front panel 14 is separated from the rear panel 16. Located on the front panel 14 is a display 18. A display is a device that gives information in a visual form, such as, for example, a liquid crystal display. A typical display suitable for use in this invention comprises a three-digit readout that represents the concentration of blood glucose, which is the result of a glucose monitoring test. The digits are typically 0.2 inch to one inch in height. The display may also provide other information to the user, with the same elements, such as cues on how to proceed with a glucose monitoring test, time of day, date of month, error information, and the like. This type of display is well known to one of ordinary skill in the art and is described, for example, in *Encyclopedia of Chemical Technology,* Vol. 15, 4th Edition, John Wiley & Sons, Inc. (1995), pages 403–406, incorporated herein by reference. Also located in the front panel 14 is a switch 20 for recalling the calibration code of the glucose monitoring device, to recall stored glucose values, to set the time and the date, to set language options, and the like. At the top end 22 of the housing 12 is a port 24, into which a test strip can be inserted for determining the blood glucose level. The port is either an electrical connector for biosensor-type glucose test strips or is an optical receptacle for photometric -type glucose test strips. A test strip is inserted into the port for the purpose of performing a glucose test. Test strips are well known to one of ordinary skill in the art and are described for example in U.S. Pat. Nos. 5,352, 351; 5,565,085; and 5,628,890, all of which are incorporated herein by reference. The surface of the housing 12 comprises a phosphorescent material. This material can be applied to the surface of the housing in the form of a coating. Alternatively, the housing can be molded from a phosphorescent material, in which case the housing would be impregnated with phosphorescent material. The glucose monitoring device 10 further comprises a light 26 that can be aimed at a test strip 28 when the test strip 28 is inserted into the port 24. Preferably, this light 26 is recessed into the housing 12, but it can also project from the surface of the housing 12. FIG. 4 shows a glucose monitoring device suitable for use in the present invention.

Figure 5:
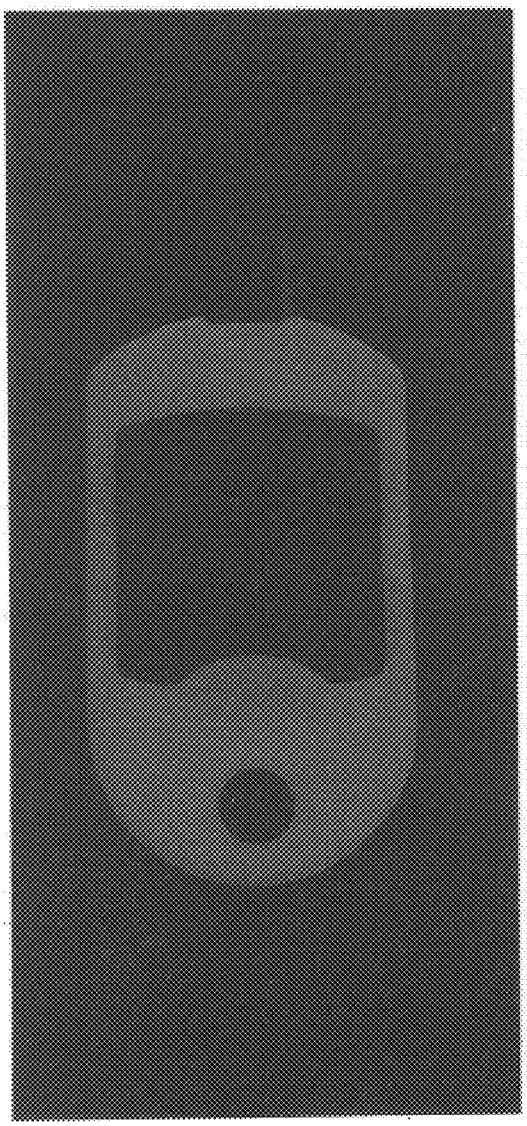
FIG. 5 is a photograph showing the glucose monitoring device of FIG. 4 treated with phosphorescent material to enable it to glow in the dark.

Colors for the phosphorescent material can be selected on the basis of the color desired in visible light and on the basis of the color desired in the absence of visible light, i. e., partial or complete darkness. Representative examples of suitable phosphorescent colors include, but are not limited to, red, orange, yellow, green, and blue. The particular colors selected for the presence of visible light and absence of visible light are not critical and are merely a matter of choice. FIG. 5 shows a glucose monitoring device in which the phosphorescent color is green.

It is preferred that the exterior surface of the housing 12 contain sufficient phosphorescent material to satisfy the following conditions:

(1) the exterior surface of the housing 12 will phosphoresce for a time sufficient to make it practical to use for several hours, e. g., two to eight hours, after exposure to the incident radiation;

(2) the exterior surface of the housing 12 retain its ability to phosphoresce for the life of the glucose monitoring device;

(3) the surface of the housing will contain a sufficient amount of phosphorescent material to enable the housing to phosphoresce at a sufficiently high intensity to make it locatable and practical for use in complete darkness.

As a practical matter, it is preferred that the amount of phosphorescent material in the composition for preparing molded plastic parts range from about 5% to about 20% by weight. It is preferred that the phosphorescent pigment particle size range from about 20 μm to about 40 μm, in order to achieve a practical and usable level of light output.

The phosphorescent material can be activated by exposing it to light having a wavelength or wavelengths of about 550 nm or lower. Illumination that is typically found in residential, commercial, industrial, or natural environments is suitable for activating the phosphorescent material contemplated for use in this invention.

The phosphorescent material can be applied to the exterior surface of the housing 12 in the form of a pigment in a carrier by means of a conventional coating or painting technique. Such techniques are described, for example, in *Encyclopedia of Chemical Technology,* Vol. 6, 4th Edition, John Wiley & Sons, Inc. (1993), pp. 606–669, incorporated herein by reference. Alternatively, the phosphorescent material can be introduced into polymeric material from which the housing 12 is formed or molded. Then, a certain percentage of the phosphorescent material will be disposed on the exterior surface of the housing 12.

Phosphorescent materials that are suitable for use in this invention include, but are not limited to, alkaline earth metal aluminate oxide doped with Europium ($XO.Al_2O_3$:Eu) and alkaline earth metal silicate oxide doped with Europium ($XO.SiO_2$:Eu), where X represents one or more elements selected from the group consisting of Ca, Mg, Sr, Ba, Zn. Alternatively, zinc sulfide can be used in place of the aforementioned phosphorescent materials.

Figure 6:
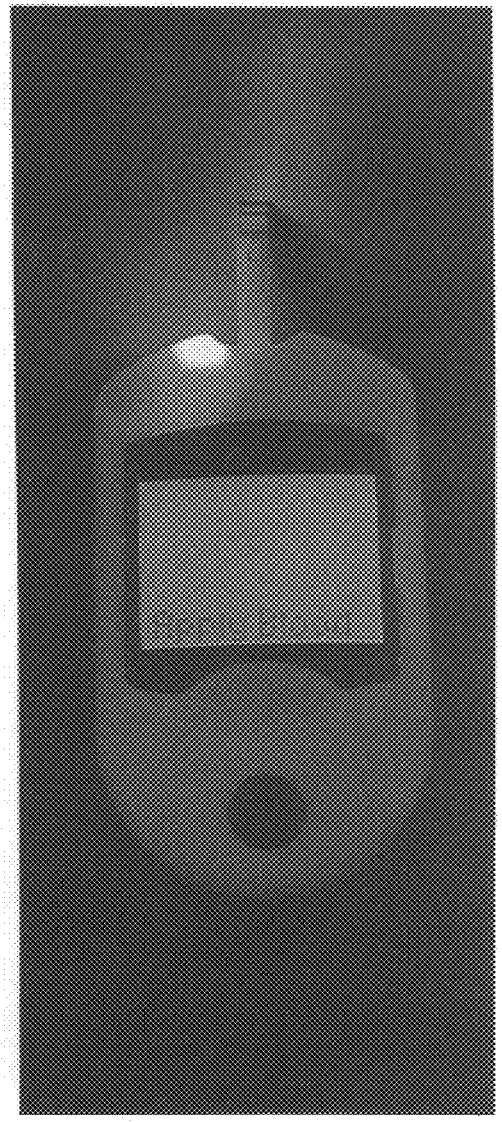
FIG. 6 is a photograph showing the glucose monitoring device of FIG. 5 wherein the port/test strip light is activated.

The light 26 for illuminating the test strip 28 is positioned so that it can provide proper illumination of the portion of the test strip 28 where the blood sample is to be deposited. It is preferred that the light 26 not only be capable of illuminating the portion of the test strip 28 where the blood sample is to be deposited but also be capable of illuminating the port 24 where the test strip 28 is to be inserted. It is preferred that the wavelength or wavelengths of the light from the light 26 be 550 nm or lower so that the light 26 can be used to expose the phosphorescent material and provide light of visible wavelength to the user of the glucose monitoring device. Alternatively, the wavelength or wavelengths of the light from the light 26 can be greater than 550 nm if the light is not required to excite the phosphorescent material. The output of the light 26 typically ranges from about 10 to about 1500 millicandelas. A light suitable for use as the test strip light 26 for the glucose monitoring device of this invention is a LED (light emitting diode) having a minimum output of 260 millicandelas, preferably 650 candelas, a forward current of 20 milliamperes, a wavelength of 470 nm, and set at an angle of about 30° from the portion of the test strip 28 where the blood sample is to be deposited. Such a LED is commercially available from Panasonic, part number LNG901CFBW. Other lights suitable for use as the test strip light 26 include incandescent bulbs and electroluminescent lamps. FIG. 6 shows a glucose monitoring device in which a light corresponding to the light 26 illuminates a test strip corresponding to the test strip 28.

There are several suitable ways for mounting the light 26. If the housing 12 is made of a translucent material, the light 26 can be mounted in the interior of the housing 12, so long as the light 26 provides sufficient output. If the housing 12 is not made of a translucent material, the light 26 can be mounted in the interior of the housing 12 so long as there is an optically transparent element, such as a lens, between the light 26 and the test strip 28. The lens would be mounted in the wall 30 of the housing 12. Alternatively, an opening 32 can be formed in the housing 12 between the light 26 and the test strip 28. Such an opening could be used whether or not the housing 12 is made of a translucent material. In another alternative embodiment, the light 26 can be mounted in the wall 30 of the housing 12. In still another alternative embodiment, the light 26 can be mounted on the exterior surface of the housing 12. The angle of illumination of the light 26 from the test strip 28 should be such that the light 26 provides proper illumination of the portion of the test strip 28 where the sample of blood is to be applied and, if desired, the port 24. FIG. 1 and FIG. 6 illustrate one of the numerous embodiments wherein the light 26 can be focused on the port 26 and the test strip.

A switch 34 for activating the light 26 can be placed in any position on the housing for the convenience of the user. For example, the switch for activating light 26 can be placed near the port 24 on the exterior surface of the housing 12. Alternatively, the light 26 can be activated by the insertion of the test strip 28 in the port 24, whereby a hidden switch is activated automatically. However, the patient may find it difficult to locate the port 24 in partial or total darkness. The source of power (not shown) for the light 26 can be disposed in the interior of the housing 12.

Figure 7:
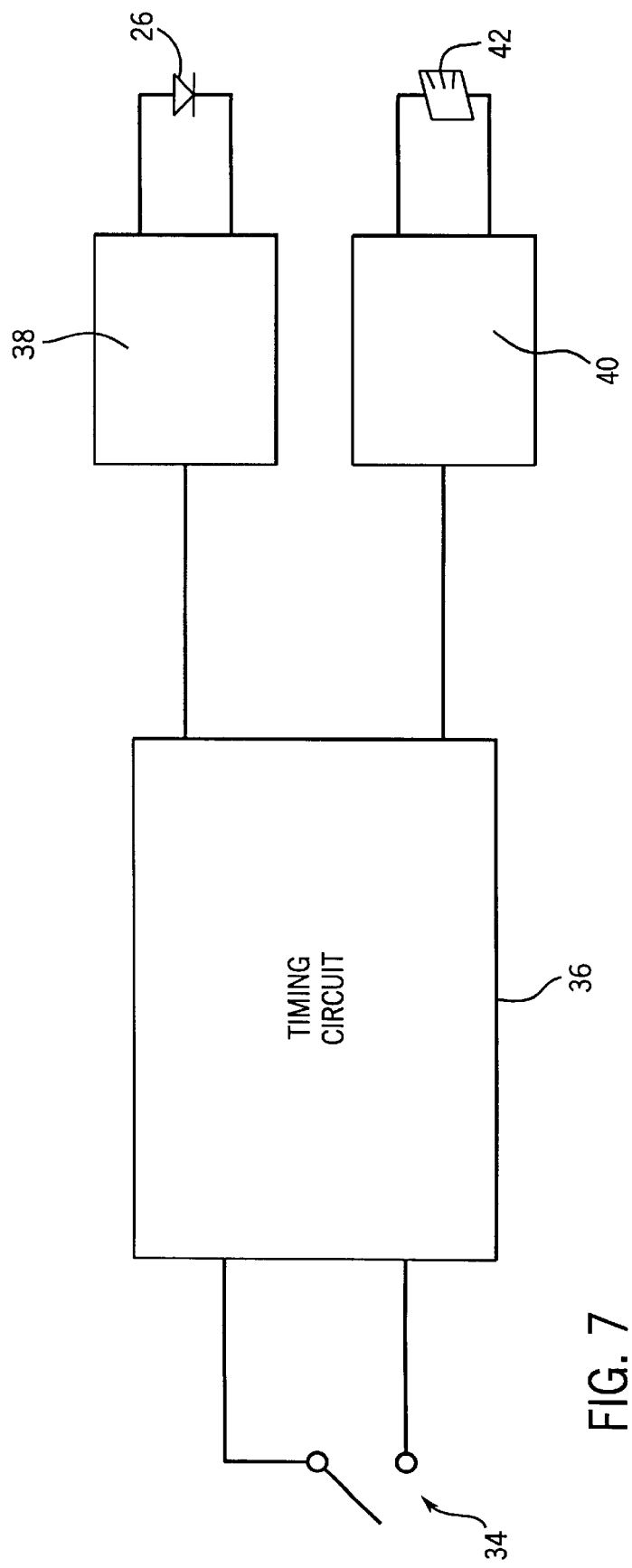
FIG. 7 is a diagram showing a type of circuit suitable for the port/test strip light.

The light 26 is preferably controlled by a series of switches and circuits of the types shown in FIG. 7. In FIG. 7, the switch 34 activates a timing circuit 36. In this type of circuit, the light 26 remains on for a fixed period of time after activation, typically about 30 seconds, or some other period of time, which should be sufficiently long to allow for obtaining a sample of blood, applying the sample of blood to the test strip, and obtaining the result. The timing circuit 36 is connected to both (1) a drive circuit 38 for the test strip light 26 or port light or both and (2) a drive circuit 40 for a light 42 for the display 18.

The display 18 is preferably backlit so that the patient can easily read the results of the test. The source of the backlighting can be electroluminescent, light emitting diode, incandescent, fluorescent, or the like. The display backlight (not shown) can be used as the light 26 to illuminate the test strip 28 and the port 24, but need not be. The display backlight can be activated in the same manner as the light 26 described previously, such as, for example, by a switch (not shown) on the exterior of the housing 12 or by the test strip 28 being inserted into the port 24. The display backlight can be of any wavelength in the visible region of the spectrum.

The following non-limiting example will further illustrate cetain aspects of the invention.

EXAMPLE

This example illustrates a formulation for preparing the housing 12 of the glucose monitoring device of this invention. Phosphorescent pigments can be mixed in a powdered resin, preferably a transparent powdered resin, such as, for example, polyethylene tetrafluorethylene, polymethylmethacrylate, epoxy resin, polyvinyl chloride. Other resins suitable for use in this invention include blends of resins, such as, for example, the blends PPG/PPB, PEG/PEB, and ABSG/ABSB. Phosphorescent pigments suitable for this invention include those available from Global Trade Alliance (Scottsdale, Arizona), such as those designated PLO (yellow-green color) and SB-8 (blue color). However, yellow-green is preferred for mixing in a polymeric material. The concentration of pigment to be used preferably ranges from about 1% to about 40%, more preferably from about 5% to about 20%, by weight of pigment.

The size of the pigment particles is preferably C size (20 to 40 $\mu$m) or D size (10 to 15 $\mu$m), more preferably D size. Lubrication agents that are suitable for the pigment/polymer mix include stearic acid acyl amine and EBS. Stearic acid acyl amine is preferred for use with polyethylene and polypropylene. EBS is preferred for use with ABS, polystyrene, polycarbonate, AS, polymethylmethacrylate. The concentration of lubrication agent typically ranges from about 0.2% to about 1%, depending on the lubrication agent used. For stearic acid acyl amine, the preferred concentration is 0.2%; for EBS, the preferred concentration is about 1%.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A glucose monitoring device comprising a housing, said housing enclosing components that determine the blood glucose level of a blood sample on a test strip, said housing having a surface, said surface comprising a phosphorescent material, said device further comprising a display, said display having a backlight, said device further comprising a test strip light, said test strip light positioned in such a way so that when said test strip light is activated, said test strip light illuminates both a port in said housing that is capable of receiving a test strip and at least a portion of a test strip when said test strip is inserted in said port in said housing.

2. The device of claim 2, wherein said test strip light, when activated, provides energy for activating said phosphorescent material.

3. The device of claim 2, wherein said test strip light is mounted in the interior of said housing.

4. The device of claim 2, wherein said test strip light is mounted on the exterior of said housing.

5. A glucose monitoring device comprising a housing, said housing enclosing components that determine the blood glucose level of a blood sample on a test strip, said housing having a surface, said surface comprising a phosphorescent material, said device further comprising a display, said display having a backlight, said device further comprising a test strip light, said test strip light positioned in such a way so that when said test strip light is activated, said test strip light illuminates both a port in said housing that is capable of receiving a test strip and at least a portion of a test strip inserted in said port in said housing, wherein said test strip light, when activated, provides light having a wavelength or wavelengths of 550 nm or less to excite said phosphorescent material.

6. The device of claim 2, wherein said phosphorescent material is applied only on the exterior surface of said housing.

7. The device of claim 2, wherein said phosphorescent material is mixed with the polymeric material from which said housing is formed or molded.

* * * * *

UNITED STATES PATENT AND TRADEMARK OFFICE
CERTIFICATE OF CORRECTION

PATENT NO. : 6,514,460 B1
DATED : February 4, 2003
INVENTOR(S) : Charles Fendrock It is certified that error appears in the above-identified patent and that said Letters Patent is hereby corrected as shown below:

Column 6,
Lines 39 and 42, replace "claim 2" with -- claim 1 --.
Lines 44, 59 and 62, replace "claim 2" with -- claim 1 --.

Signed and Sealed this

Twenty-second Day of July, 2003

JAMES E. ROGAN
*Director of the United States Patent and Trademark Office*